US007544505B2

(12) United States Patent
Jung et al.

(10) Patent No.: US 7,544,505 B2
(45) Date of Patent: Jun. 9, 2009

(54) HYBRIDIZATION CHAMBER AGITATION DEVICE USING PUMP AND VALVES

(75) Inventors: Sung-ouk Jung, Gyeonggi-do (KR); Nam Huh, Seoul (KR); Soo-suk Lee, Gyeonggi-do (KR); Chang-eun Yoo, Seoul (KR); Hun-joo Lee, Seoul (KR)

(73) Assignee: Samsung Electronics Co., Ltd. (KR)

( * ) Notice: Subject to any disclaimer, the term of this patent is extended or adjusted under 35 U.S.C. 154(b) by 272 days.

(21) Appl. No.: 11/295,844

(22) Filed: Dec. 6, 2005

(65) Prior Publication Data

US 2006/0147960 A1 Jul. 6, 2006

(30) Foreign Application Priority Data

Dec. 6, 2004 (KR) ...................... 10-2004-0101650

(51) Int. Cl.
*C12M 1/34* (2006.01)

(52) U.S. Cl. .................................................. 435/287.2

(58) Field of Classification Search ............... 435/287.2
See application file for complete search history.

(56) References Cited

U.S. PATENT DOCUMENTS

| | | | | |
|---|---|---|---|---|
| 6,391,623 | B1 | 5/2002 | Besemer et al. | 435/287.2 |
| 2002/0001803 | A1 | 1/2002 | Smith et al. | 435/6 |
| 2003/0013184 | A1 | 1/2003 | Streit et al. | 435/287.2 |
| 2004/0209354 | A1 * | 10/2004 | Mathies et al. | 435/287.2 |
| 2006/0160205 | A1 * | 7/2006 | Blackburn et al. | 435/287.2 |

FOREIGN PATENT DOCUMENTS

| | | | |
|---|---|---|---|
| EP | 0 933 126 | A1 | 8/1999 |
| KR | 1020040039981 | A | 5/2004 |
| WO | WO 03/015923 | A1 | 2/2003 |

OTHER PUBLICATIONS

European Search Report; Application No. EP 05 02 5460; Date: Jun. 22, 2006.

* cited by examiner

*Primary Examiner*—Walter D Griffin
*Assistant Examiner*—Lydia Edwards
(74) *Attorney, Agent, or Firm*—Cantor Colburn LLP

(57) ABSTRACT

Provided is an agitation device used to agitate a solution in a hybridization chamber, the agitation device including: the hybridization chamber; first and second air channels connected to ends of the hybridization chamber; a first valve disposed in the first air channel; a second valve disposed in the second air channel; an integrated air channel connecting the first and second air channels; and a pump disposed in the integrated air channel. The agitation device is suitable for effective diffusion of a sample when performing hybridization using a DNA chip. Therefore, a probe can be effectively hybridized with a target material.

11 Claims, 9 Drawing Sheets

HYBRIDIZATION CHAMBER AGITATION DEVICE USING PUMP AND VALVES

CROSS-REFERENCE TO RELATED PATENT APPLICATIONS

This application claims the benefit of Korean Patent Application No. 10-2004-0101650, filed on Dec. 6, 2004, in the Korean Intellectual Property Office, the disclosure of which is incorporated herein in its entirety by reference.

BACKGROUND OF THE INVENTION

1. Field of the Invention

The present invention relates to a hybridization chamber agitation device of a biochip, and more particularly, to an agitation device used to effectively agitate a solution in a hybridization chamber and a method of agitating using the same.

2. Description of the Related Art

A biochip is formed by affixing on a support a bimolecular probe to be analyzed with high density. The biomolecular probe may be DNA, protein, or the like. By detecting whether the probe is hybridized with a target material contained in a sample, genetic expression profile, genetic defects, protein distribution, reaction characteristics, or the like can be analyzed. Biochips are categorized into DNA chips, protein chips, and the like according to the type of probes used. In addition, biochips are categorized into micro-array chips affixed on solid supports and lab-on-a-chips affixed on microchannels according to affixed subjects. Agitation and washing/drying systems are needed to attain effective hybridization between the target material contained in the sample, and the probe.

Conventional hybridization systems can be categorized into hybridization systems using pumps and hybridization systems using air and a solution. Examples of hybridization systems using pumps include a hybridization system using two membrane pumps disclosed in US Patent Publication No. 2003/0013184 in the name of Tecan, and a hybridization system using a flow system pump disclosed in U.S. Pat. No. 6,391,623 in the name of Affymetrix. Examples of hybridization systems using air and a solution include a hybridization system using a rotary oven disclosed in EP Patent No. 0933126 and a hybridization system using a rotary cartridge disclosed in US Patent Publication No. 2002/0001803.

In the conventional hybridization system using a flow system pump disclosed in U.S. Pat. No. 6,391,623 in the name of Affymetrix, illustrated in FIGS. 1A and 1B, a hybridization chamber is connected to a pump by a fluid delivery system, and hybridization is facilitated by the circulation of a fluid. In this case, however, the amount of the sample used must be large due to the use of a peristaltic pump and a circulation fluid channel. Because of this, after hybridization is performed for 16 hours using the hybstation, a used DNA chip must be washed and dried using a rotary oven.

In the conventional hybridization system using two membrane pumps disclosed in US Patent Publication No. 2003/0013184 filed by Tecan, illustrated in FIGS. 2A and 2B, two channels are connected to ends of the hybridization chamber. Each of the channels includes an agitation membrane and two micro pumps such that the target solution can be effectively hybridized with the probe on a chip. However, in order to obtain effective agitation in the chamber, the target solution is filled up to a chamber cover to mix the sample. Therefore, chamber is more contaminated.

The conventional hybridization system disclosed in EP Patent No. 0933126, illustrated in FIG. 3, uses a rotary oven. In this case, hybridization is performed in the rotary oven for 16 hours. The period for hybridization may vary according to chip contents.

In the conventional hybridization system using a rotary cartridge disclosed in US Patent Publication No. 2002/0001803, as illustrated in FIGS. 4A and 4B, the hybridization is performed by rotating the cartridge. That is, after a chip cartridge is manufactured, a centrifugal force is used for hybridization.

A conventional memorec A-hyb illustrated in FIG. 5 uses an active circulation by using a diaphragm pump. In this case, the amount of the sample used must be large, for example, about 220 μl, because the sample is circulated.

In order to solve these problems, the inventors of the present invention have confirmed that an agitation device can be effectively agitated by using a single pump and two valves disposed in an integrated channel and completed the present invention.

SUMMARY OF THE INVENTION

The present invention provides an agitation device in which the amount of a sample required is decreased and a solution contained in a hybridization chamber is effectively hybridized.

The present invention also provides a method of effectively agitating a solution contained in the hybridization chamber using the agitation device.

According to an aspect of the present invention, there is provided an agitation device used to agitate a solution in a hybridization chamber, the agitation device including: the hybridization chamber; first and second air channels connected to ends of the hybridization chamber; a first valve disposed in the first air channel; a second valve disposed in the second air channel; an integrated air channel connecting the first and second air channels; and a pump disposed in the integrated air channel.

Biomolecules selected from DNA, RNA, Peptide Nucleic Acid (PNA), Locked Nucleic Acid (LNA), peptide, and protein are hybridized using the agitation device. one of the biomolecules may act as a probe, being affixed on a solid substrate, and the other biomolecule may act as a target material and be contained in a solution.

The hybridization chamber of the agitation device may be fixed in the agitation device, and is preferably a separable cartridge. A biochip, that is, a solid substrate on which probe molecules are fixed, may be inserted into the cartridge.

Any valve that can be opened and closed in response of electric signals can be used in the present invention. Preferably, a solenoid valve (series 075P obtained from bio-chem-valve Co.) can be used.

Any pump that can operate in response of electric signals can be used in the present invention. In particular, the pump may be a stepping motor-type micro pump.

According to another aspect of the present invention, there is provided a method of agitating a solution in a hybridization chamber using an agitation device including: the hybridization chamber; first and second air channels connected to ends of the hybridization chamber; a first valve disposed in the first air channel; a second valve disposed in the second air channel; an integrated air channel connecting the first and second air channels; and a pump disposed in the integrated air channel; the method including: pumping away from a pump when the first valve is opened and the second vale is closed; pumping toward the pump when the first valve is closed and the second valve is closed; pumping away from the pump when the first valve is closed and the second valve is closed; and pumping toward the pump when the first valve is closed and the second valve is opened.

The agitation method according to the present invention and a conventional agitation method using the circulation of a solution in the hybridization chamber are different from each other in that in the present invention the solution contained in the hybridization chamber is not circulated and mixed by air in the air channel in a closed system. Therefore, the amount of the sample can be decreased to perform hybridization.

The break period between periods of pumping toward the pump may be in the range of 1 to 3 minutes. The presence of the break period results in an increase of hybridization efficiency and a constant hybridization chip intensity coefficient variation (CV).

The hybridization system may be constructed such that the solution contained in the hybridization chamber flows in a closed system by pumping away from and toward the micro pump and selectively closing the valves. Thus, the target solution can be effectively diffused onto the chip and bound to the probe affixed on the chip.

Although the size of the pump can be varied, the sizes of the valves and the pump may be a few to several tens of μms for ease of using the micro array and the lab-on-a-chip.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, embodiments of the present invention will be described in detail with reference to the appended drawings.

Figure 1A:
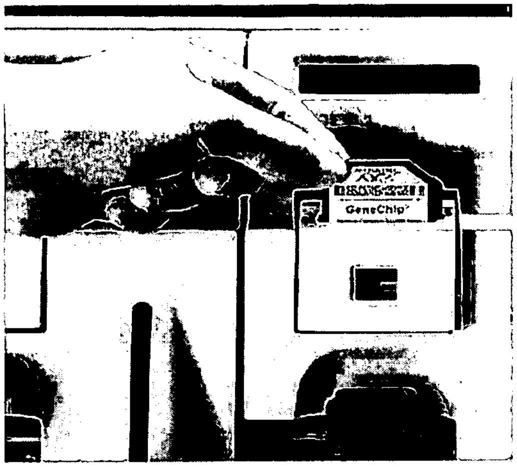
FIGS. 1A and 1B are views of a conventional hybridization device obtained from Affymetrix Co.
Figure 1B:
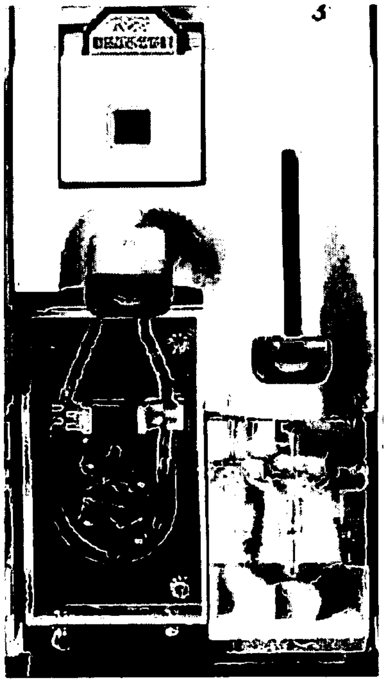
Figure 2A:
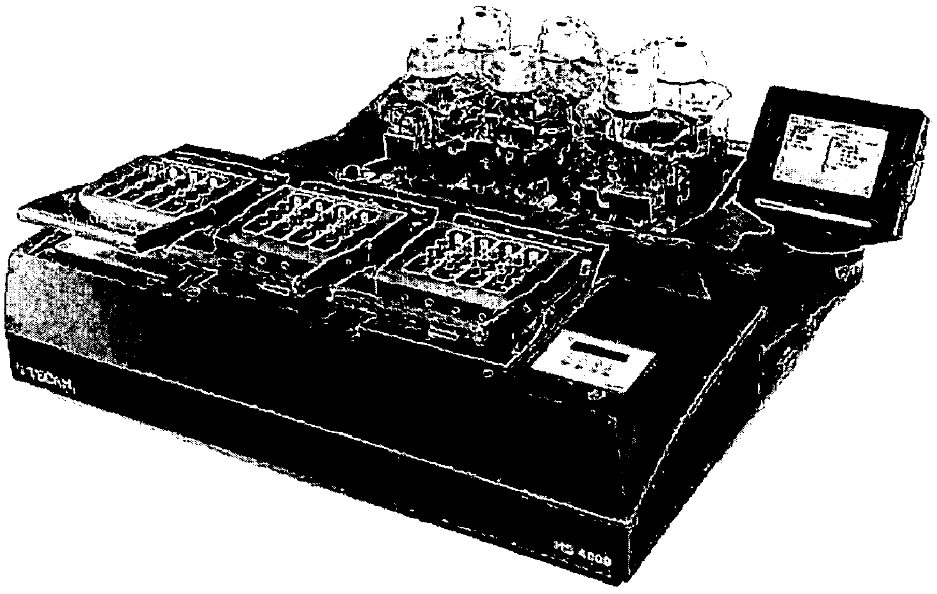
FIGS. 2A and 2B are views of a conventional hybridization device obtained from Tecan Co.
Figure 2B:
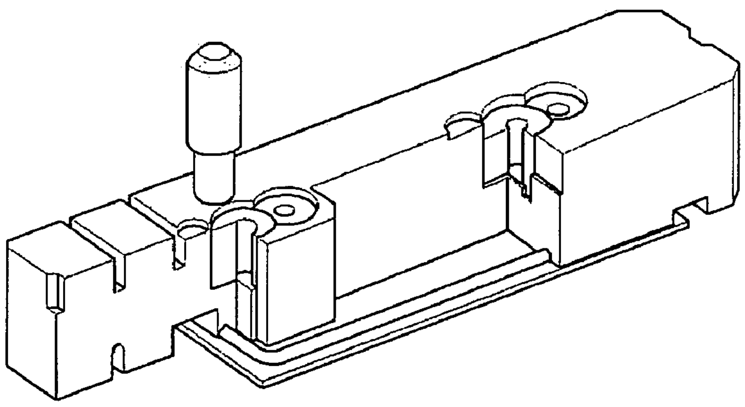
Figure 3:
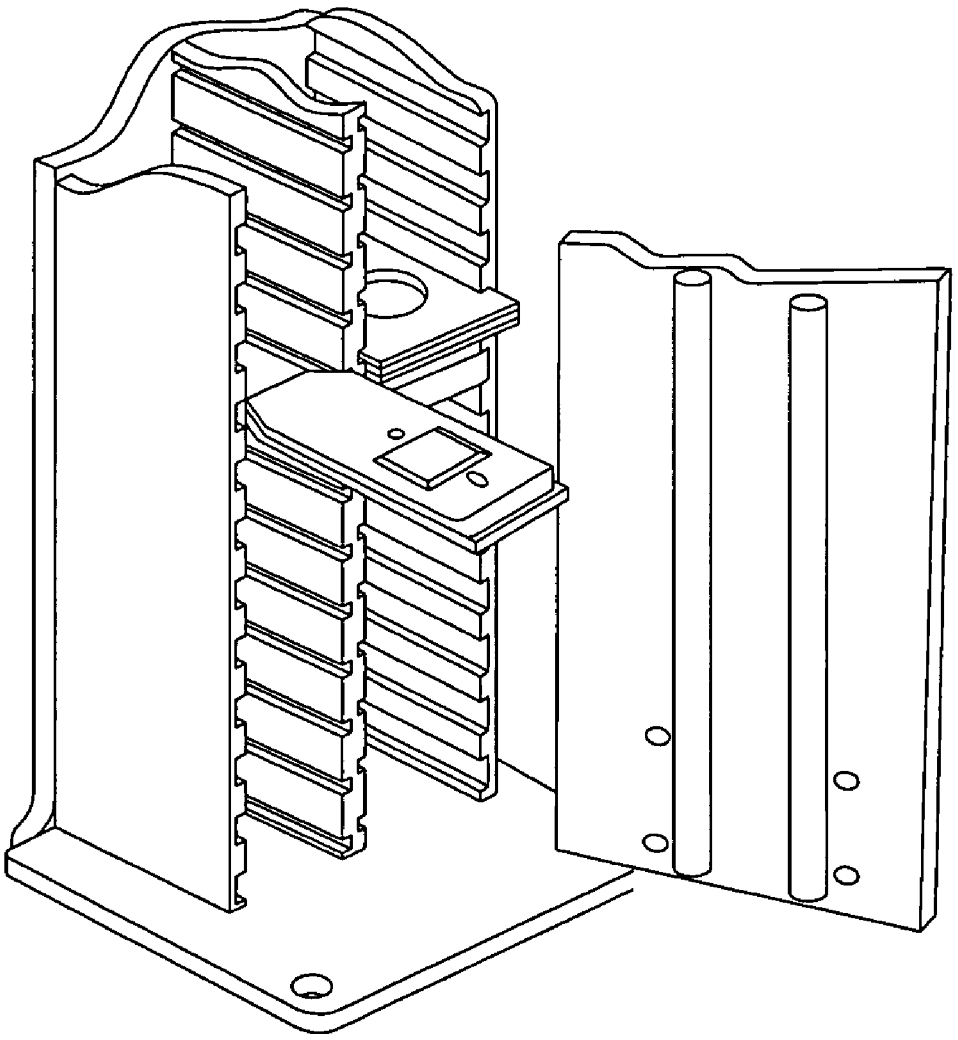
FIG. 3 is a view of a conventional hybridization device including a rotary oven.
Figure 4A:
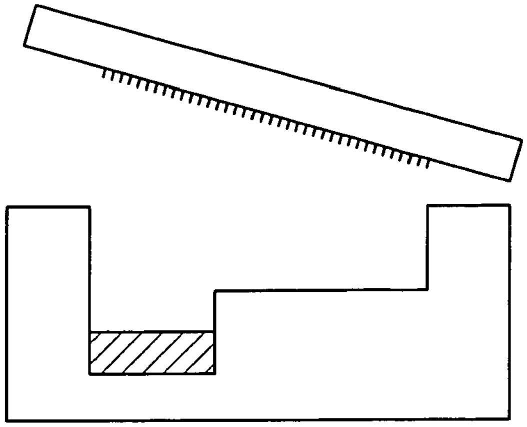
FIGS. 4A and 4B are views of a conventional hybridization device including a rotary cartridge.
Figure 4B:
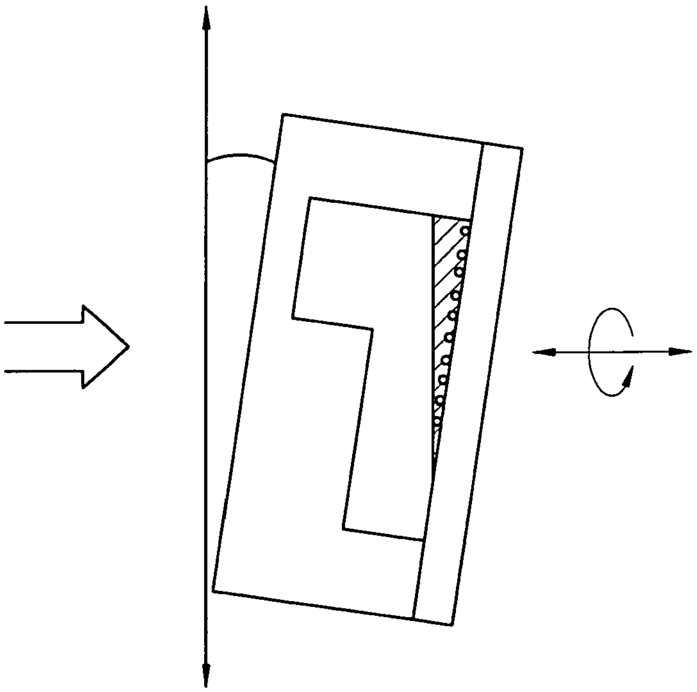
Figure 5A:
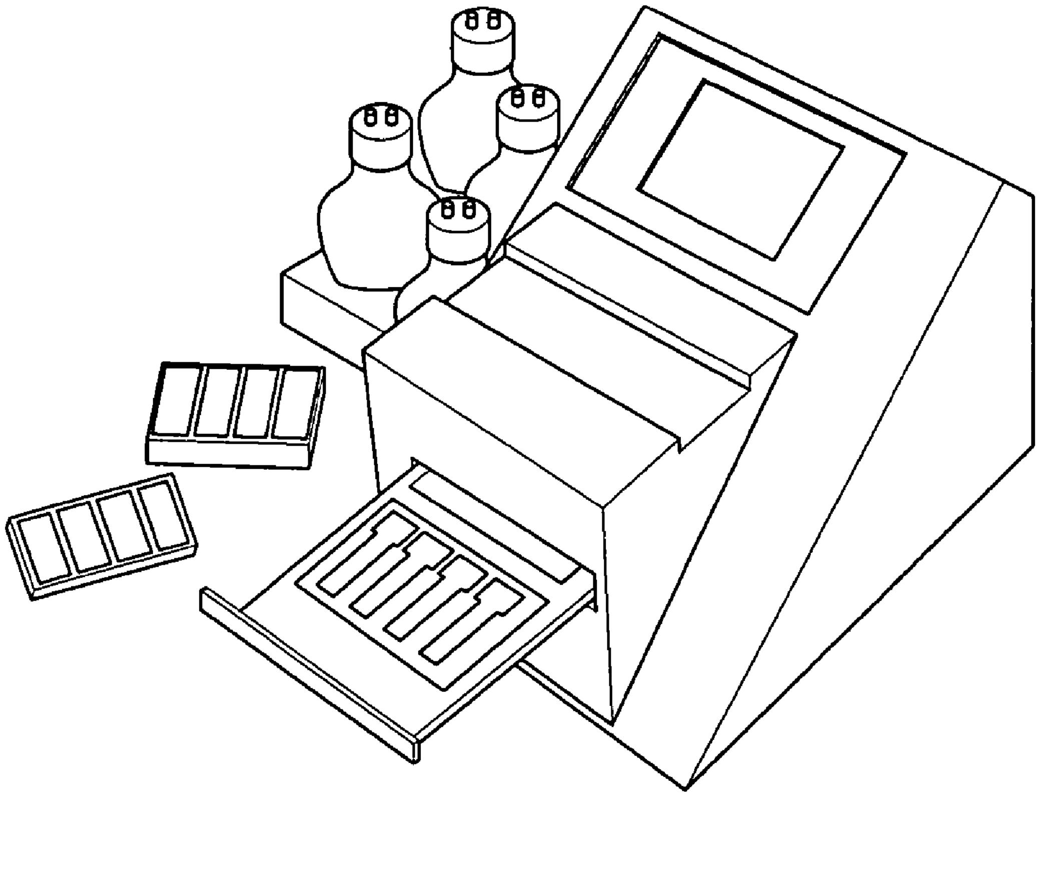
FIGS. 5A and 5B are views of a conventional hybridization device using active circulation obtained from Memorec. Co.
Figure 5B:
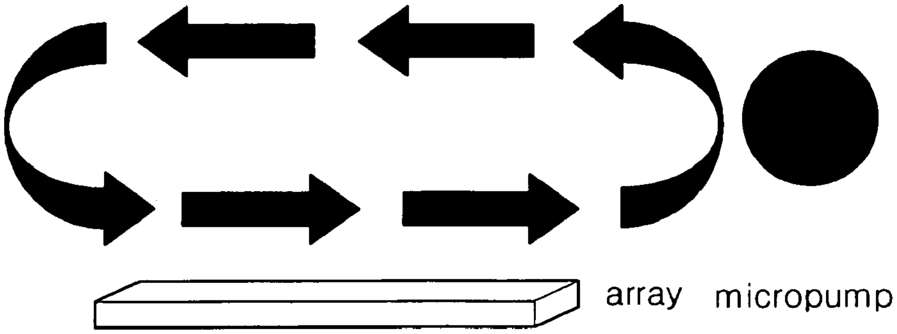
Figure 6:
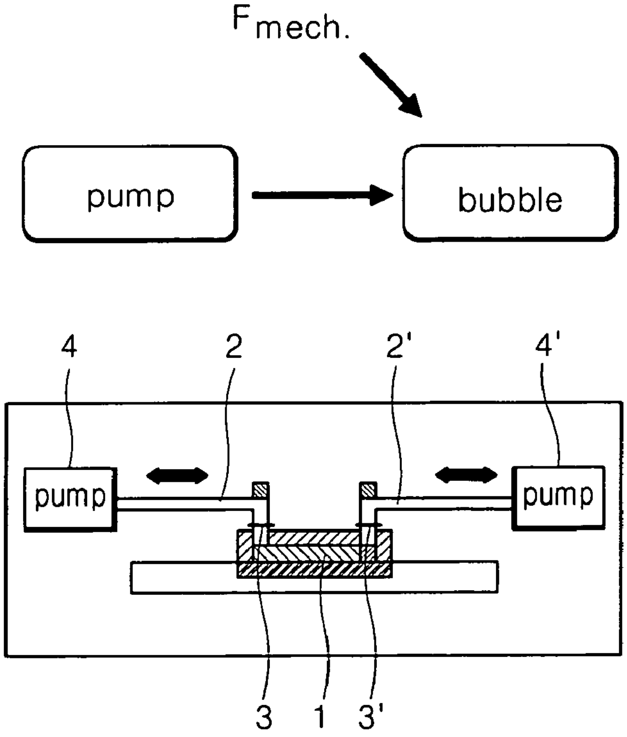
FIG. 6 is a schematic view of a conventional hybridization device obtained from Tecan Co.

FIG. 6 is a schematic view of a conventional hybridization device obtained from Tecan Co. Referring to FIG. 6, a hybridization chamber 1 has two ends respectively connected to channels 2 and 2'. The channels 2 and 2' are separated from the hybridization chamber 1 by membranes 3 and 3' such that contamination of the hybridization chamber 1 is prevented. An end of each of the channels 2 and 2' is connected to pumps 4 and 4'. A mechanical force applied to the pumps 4 and 4' pumps air inside the channels 2 and 2'. The pumped air agitates a solution contained in the hybridization chamber 1 through the membranes 3 and 3'. In this case, the membranes 3 and 3' must be included because the channels 2 and 2' can be contaminated due to the difficulty of precisely adjusting the force generated by the pumps 4 and 4'.

Figure 7:
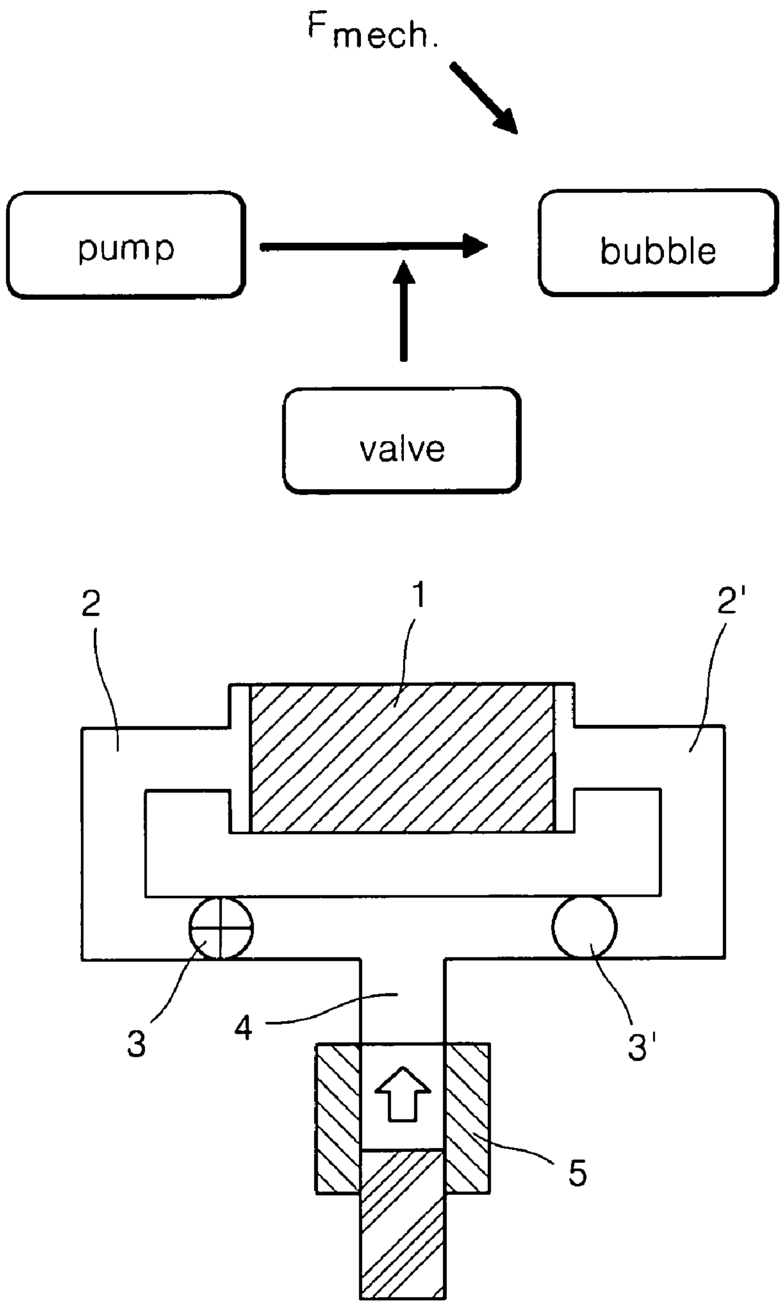
FIG. 7 is a schematic view of an agitation device used to agitate a solution in a hybridization chamber according to an embodiment of the present invention.

FIG. 7 is a schematic view of an agitation device used to agitate a solution in a hybridization chamber according to an embodiment of the present invention. Referring to FIG. 7, the agitation device according to an embodiment of the present invention includes a hybridization chamber 1, air channels 2 and 2' respectively connected to ends of the hybridization chamber 1, valves 3 and 3' respectively disposed in the air channels 2 and 2', an integrated air channel 4 connecting the air channels 2 and 2', and a pump 5 disposed in the integrated air channel 4. The hybridization device according to an embodiment of the present invention is different from the hybridization device obtained from Tecan Co. in that the hybridization device according to an embodiment of the present invention includes a 3-way valve that allows the flow of bubbles to be controlled by a single pump instead of two syringe pumps. Therefore, manufacturing costs are decreased, and contamination of the air channels 2 and 2' can be prevented as a result of the use of the single pump such that membranes are not needed.

Figure 8:
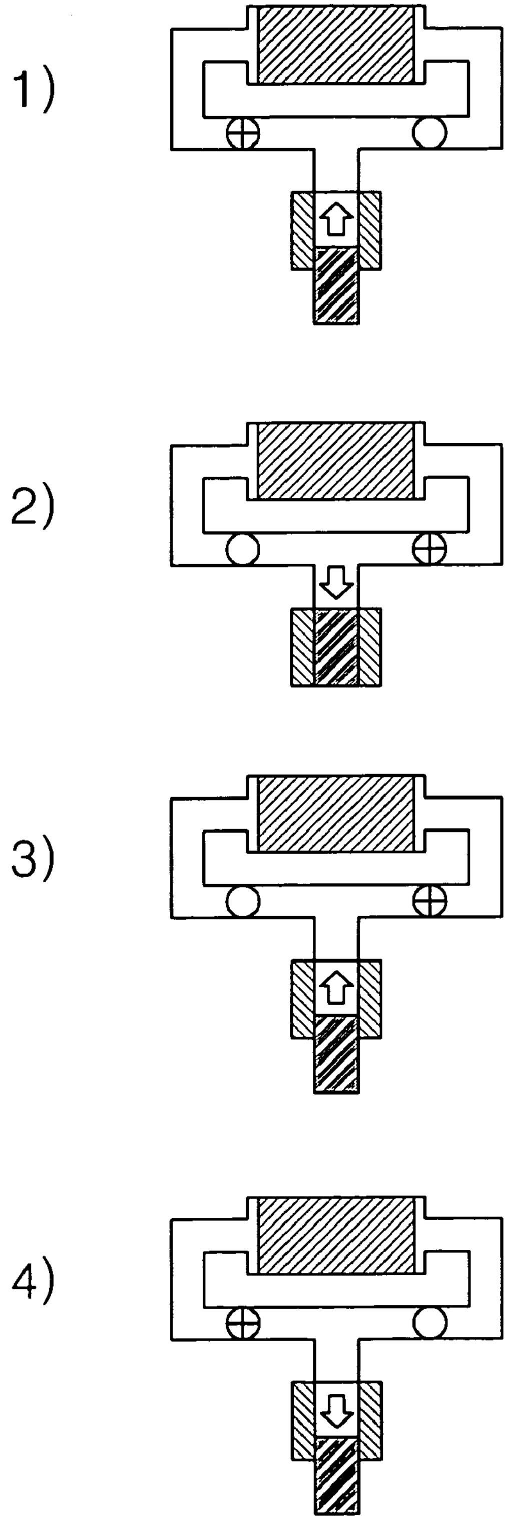
FIG. 8 is a schematic diagram illustrating a method of agitating a hybridization chamber according to an embodiment of the present invention.

FIG. 8 is a schematic diagram illustrating a method of agitating a hybridization chamber according to an embodiment of the present invention. Referring to FIG. 8, the method includes: pumping air from a pump when one of the two valves is opened and the other valve is closed (illustrated in operation 1 of FIG. 8); pumping air to the pump when the opened valve and the closed valve are reversed (illustrated in operation 2 of FIG. 8); pumping air from the pump when no changes are made on the valves (illustrated in operation 3 of FIG. 8); and pumping air to the pump when the closed valve and the opened valve are again reversed (illustrated in operation 4 of FIG. 8). In FIG. 8, a closed valve is represented by a circle with '+' therein, an opened valve is represented by a circle, and changes in a filled portion of the hybridization chamber indicates movement of the solution. A solution contained in the hybridization chamber is agitated by repeating these operations.

Hereinafter, the present invention will be described in detail by explaining exemplary embodiments of the invention.

EXAMPLE 1

Diffusion Time During Standing and Agitation

An acryl structure into which a cartridge can be inserted was manufactured. A chamber was covered by a sealing pad and then the sealing pad was fixed by screws, forming the chamber with a height of 150 μm. The sealing pad was connected to two valves (series 075P obtained from bio-chem-valve Co.) and a pump (a stepping motor type pump obtained from uniflow Co.) via holes formed in the sealing pad, thus forming an agitation device according to an embodiment of the present invention illustrated in FIG. 7. 45 μl of deionized (DI) water and 1 μl of ink were sequentially added to the completed structure via an inlet hole of the completed structure, and then the completed structure was connected to an agitation pump. Diffusion was measured by repeatedly alternating pumping directions with various pumping speeds.

A square chamber with a diameter of 17.3 mm and a height of 150 μm was filled with DI water, and then 5 μl of ink was added to the square chamber. Diffusion times were measured by repeatedly alternating pumping directions with various pumping speeds. A volume pumped from the pump was fixed at 4 μl and the period for which pumping direction is away from the pump was changed, thus changing the agitation rate.

Diffusion times and agitation rates are shown in Table 1.

TABLE 1

| Agitation rate | Time required |
|---|---|
| 0 ml/min | 13 hr |
| 0.12 ml/min | 25 min |
| 0.24 ml/min | 10 min |
| 2.4 ml/min | 5 min |

Referring to Table 1, it can be confirmed that the diffusion rate of the sample was heavily dependent on the agitation speed.

EXAMPLE 2

Hybridization Chip Intensity Coefficient Variation (CV) According to Period for Pumping Toward Pump and Break Period Hybridization chip intensity CV according to the period when pumping occurred away from the pump and break period was measured using the agitation device manufactured in Example 1. A chip was manufactured by cutting a silicon wafer coated with amine to a size matching the acryl structure manufactured in Example 1 and affixing identical probes (sequence: TGT TCT CTT GTC TTG) on the coated silicon wafer using a spotter. The resulting chip was affixed on the acryl structure. The chip was formed in a cartridge shape using an adhering agent such that the stability of the chip affixed on the acryl structure was increased (see Korean Patent Application No. 2004-0039981). Then, a target solution manufactured by mixing a probe (CAA GAC AAG AGA ACA) labeled with Cy3 into a hybridization buffer, was added to the hybridization chamber, and then agitated using the pump. When hybridization was completed, the cartridge was washed with a 3×SSPET buffer for 5 minutes and washed with a 1×SSPET buffer for 5 minutes. Then, an image of the chip was taken using a laser scanner, each spot in the image was quantified, and the intensity CV between spots was measured. The break period is a period between subsequent periods when air is pumped away from the pump.

Figure 9:
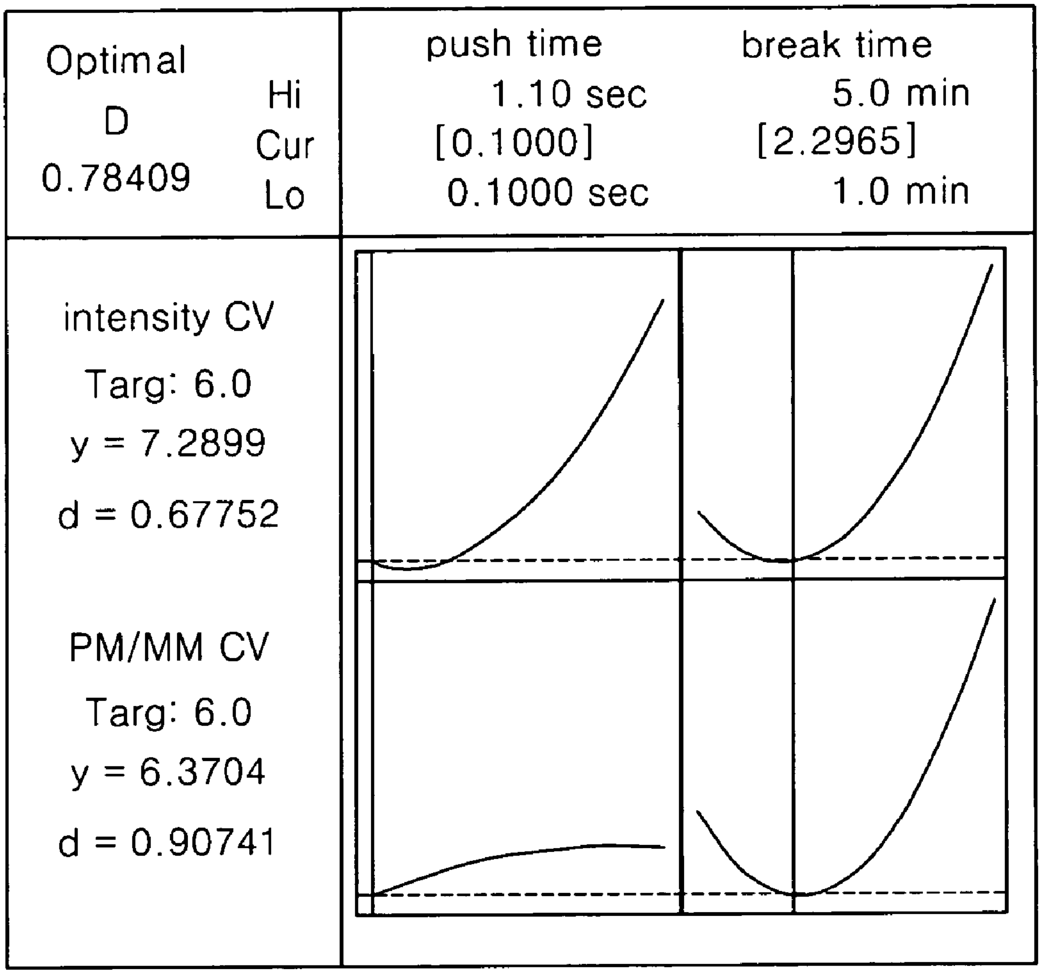
FIG. 9 illustrates graphs of the intensity coefficient variation (CV) with respect to pushing time and break period of hybridization chips manufactured in Examples of the present invention.

FIG. 9 illustrates graphs of the intensity CV of a hybridization chip with respect to the period when air was pumped away from the pump and the break period according to an embodiment of the present invention. CV is a coefficient variation and a lower CV is desirable. Referring to FIG. 9, when a volume of 4 ul was pushed, the period when air was pumped was set to 0.1 sec, and the break period was set to 2.3 minutes, spot intensity CV and PM/MM ratio CV were minimized. The break period is needed and is preferably 1 to 3 minutes.

EXAMPLE 3

Use in Hybstation System

A MODY3 chip agitated using an agitation device according to an embodiment of the present invention was compared with that agitated using a conventional cover slide patch method. In this case, probes were used as indicated in Table 2.

TABLE 2

| WP | sequence | MP | Sequence |
|---|---|---|---|
| E02-01rwp | gacttgaccatcTTCgccacacg | E02-01rmp | gacttgaccatcTCCgccacacg |
| E02-05rwp | tcccgctgtGGGatgttgtgctgc | E02-05rmp | tcccgctgtGTGatgttgtgctgc |
| E02-08rwp | tggtatcgaccACCtcccgctgt | E02-08rmp | tggtatcgaccATCtcccgctgt |
| E02-10rwp | ttgggacaggTGGgactggttgag | E02-10rmp | ttgggacaggTAGgactggttgag |

First, the probes, which correspond to a target hexane MODY3, were affixed on a substrate, thus forming a microarray. In detail, a wild probe (WP) and a mutant probe (MP) were added to a solution mixture of polyethyleneglycol (PEG), which has a molecular weight of 10,000, 0.025M (pH 10) of a sodium carbonate buffer, and formamide in a weight ratio of 1:1:2. The resulting solution was spotted on a silicon wafer using a bio-robot printer (Model No. PixSys 5500, obtained from Cartesian Technologies, Inc., CA, USA), and the silicon wafer was sit in a wet incubator at 37° C. for 4 hours. Then, the surrounding noise was controlled such that portions of the silicon wafer that were not spotted were subjected to an appropriate reaction, thereby providing a negative charge to the amine group adhered to the surface of the wafer. Therefore, adherance of the target hexane to the silicon wafer could be prevented. The resulting silicon wafer was placed in a drying device. In the present example, the body or ends of the target hexane (tgggttctgccctttgcgctgggatggtgaagcttccagcc) was tagged with Cy3-dUTP as a fluorescent material. 187 nM of the target hexane dissolved in 0.1% of a 6×SSPET solvent (Saline Sodium Phosphate EDTA Buffer containing 0.1% of Trition X-100), and the microarray reacted at 37° C. for 16 hours. Separately, 187 nM of the target hexane dissolved in 0.1% of a 6×SSPET solvent (Saline Sodium Phosphate EDTA Buffer containing 0.1% of Trition X-100), and the microarray were hybridized according to an embodiment of the present invention. Each of the chips was washed with 0.05% 6×SSPET for 5 minutes and 0.05% 3×SSPET for 5 minutes, dried at room temperature for 5 minutes, and then scanned by an Axon scanner (Model GenePix 4000B, Axon Instrument, Inc., CA, USA). The scanning data was analyzed using GenePix Pro 3.0 (obtained from Axon Instrument, Inc., CA, USA), thus obtaining ratio components and intensity components. The results are shown in Table 3.

TABLE 3

| | Hyb time | Washing time | Drying time | Amount of sample used | Note |
|---|---|---|---|---|---|
| Traditional method | 4 hr | 10 min | less than 1 min | 60 µl | the other conditions are same |
| Hybstation method | 30 min | 6 min | 30 sec | 45 µl | |

Averages of spot intensities, PM/MM ratios, and coefficient variations (CVs) were measured by testing 20 copies of chips according to a conventional method and 20 copies of chips according to hybridization system. The results are shown in Table 4.

TABLE 4

| | Reference | | Hybstation method of present invention | |
|---|---|---|---|---|
| | Spot intensity | Ratio | Spot intensity | Ratio |
| Average | 18438.55 | 2.52 | 9852.38 | 2.31 |
| CV | 32.78 | 7.05 | 13.66 | 4.69 |

Referring to Table 4, intensity CV and PM/MM ratio CV were much smaller when an agitation device according to an embodiment of the present invention was used than when a conventional reference method was used.

As mentioned above, according to the present invention, a sample can be effectively diffused when performing hybridization using a DNA chip. Therefore, a probe can be effectively hybridized with a target. In addition, in agitation device according to the present invention, the amount of the sample to be agitated for hybridization is very small, for example, about 45 ul. Therefore, the construction of the agitation device according to the present invention is inexpensive in comparison with conventional hybridization systems with two pumps. Further, in order to perform mixing in a closed system, only a pump and two valves are needed such that the agitation device according to the present invention can replace hybridization systems using a conventional Diaphragm pump or a conventional Peristaltic pump.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An agitation device used to agitate a solution in a hybridization chamber, the agitation device comprising:

the hybridization chamber;

first and second air channels connected to ends of the hybridization chamber such that when a solution is contained in the hybridization chamber the solution is in direct contact with air in the first and second air channels;

a first valve disposed in the first air channel;

a second valve disposed in the second air channel;

an integrated air channel connecting the first and second air channels; and a pump disposed in the integrated air channel such that the pump pumps away from the pump when the first valve is opened and the second valve is closed;

the pump pumps toward the pump when the first valve is closed and the second valve is closed;

the pump pumps away from the pump when the first valve is closed and the second valve is closed; and the pump pumps toward the pump when the first valve is closed and the second valve is opened.

2. The agitation device of claim 1, wherein biomolecules selected from the group consisting of DNA, RNA, Peptide Nucleic Acid (PNA), Locked Nucleic Acid (LNA), peptide, and protein are hybridized.

3. The agitation device of claim 1, wherein the hybridization chamber is a separable cartridge.

4. The agitation device of claim 1, wherein the first or second valve is a solenoid valve.

5. The agitation device of claim 1, wherein the pump is a stepping motor-type micro pump.

6. A method of agitating a solution in a hybridization chamber using an agitation device comprising:

a hybridization chamber;

first and second air channels connected to ends of the hybridization chamber such that when a solution is contained in the hybridization chamber the solution is in direct contact with air in the first and second air channels;

a first valve disposed in the first air channel;

a second valve disposed in the second air channel;

an integrated air channel connecting the first and second air channels; and a pump disposed in the integrated air channel; the method comprising:

pumping away from a pump when the first valve is opened and the second vale is closed;

pumping toward the pump when the first valve is closed and the second valve is closed;

pumping away from the pump when the first valve is closed and the second valve is closed; and pumping toward the pump when the first valve is closed and the second valve is opened.

7. The method of claim 6, wherein a solution contained in the hybridization chamber is agitated in a closed system without circulation through a channel.

8. The method of claim 6, wherein a break period between periods of pumping toward the pump is in the range of 1 to 3 minutes.

9. The method of claim 8, wherein biomolecules in a solution in the hybridization chamber are selected from the group consisting of DNA, RNA, Peptide Nucleic Acid (PNA), Locked Nucleic Acid (LNA), peptide, and protein.

10. The method of claim 6, wherein the hybridization chamber is a cartridge separable from the agitation device.

11. The method of claim 9, wherein a coefficient of variance (CV) of both a signal intensity and a PM/MM ratio is lowered.

* * * * *